United States Patent [19]
Nettekoven et al.

[11] Patent Number: 5,885,280
[45] Date of Patent: Mar. 23, 1999

[54] ELECTROSURGICAL ELECTRODE CONNECTOR

[75] Inventors: William S. Nettekoven, Sandy; Eric S. Steckel, Salt Lake City, both of Utah

[73] Assignee: MegaDyne Medical Products, Inc., Draper, Utah

[21] Appl. No.: 555,577

[22] Filed: Nov. 8, 1995

[51] Int. Cl.$^6$ .................................................. A61N 17/36
[52] U.S. Cl. .............................. 606/41; 606/34; 439/332; 439/341; 439/823; 439/909
[58] Field of Search ............... 606/32–52; 439/332–334, 439/337, 338, 341, 342, 345, 347, 891, 823, 909

[56] References Cited

U.S. PATENT DOCUMENTS

| | | |
|---|---|---|
| 176,069 | 4/1876 | Ryder . |
| 278,346 | 5/1883 | Long . |
| 490,831 | 1/1893 | Lohers . |
| 1,221,524 | 4/1917 | Frankel . |
| 1,851,843 | 3/1932 | Inman . |
| 1,869,181 | 7/1932 | Beck . |
| 1,916,722 | 7/1933 | Ende . |
| 2,554,876 | 5/1951 | Olson . |
| 3,144,804 | 8/1964 | Harwood . |
| 3,256,031 | 6/1966 | Fillweber . |
| 4,255,007 | 3/1981 | Michaels et al. ............ 439/332 |
| 4,657,016 | 4/1987 | Garito et al. ................ 606/45 |
| 5,035,695 | 7/1991 | Weber, Jr. et al. .......... 606/45 |

FOREIGN PATENT DOCUMENTS

| | | |
|---|---|---|
| 1241174 | 8/1960 | France ................... 439/345 |
| 2404764 | of 1974 | Germany . |
| WO 8202488 | 8/1982 | WIPO . |
| WO 9202272 | 2/1992 | WIPO . |

*Primary Examiner*—David M. Shay
*Attorney, Agent, or Firm*—John L. Sigalos

[57] ABSTRACT

An electrosurgical electrode connector instrument for use in rapidly and easily connecting/disconnecting a disposable electrosurgical tip to and from a non-disposable mounting body. The non-disposable body includes a rod-like extension equipped with a pair of specially shaped projecting pins each having ramps and a curved surface. These pins are positioned on opposite sides of the rod-shaped extension. The disposable electrosurgical tip is provided at its proximal end with a tunnel-like recess having a pair of longitudinally disposed slots to define a pair of bifurcated cantilevered springy wall members each fitted with a small pin-locking aperture, thus adapting the disposable tip for telescopic engagement with the rod-like extension so that the recess of the disposable tip can be slid onto the rod-like extension with the specially shaped pins spreading the springy wall members slightly. After the tunnel-like recess has fully telescoped onto the aforementioned extension, the specially shaped pins snap into the pin-locking apertures to disengageably lock them in place. When it is desired to unlock the tip, the curved surfaces of the special geometrical characteristics of the pins make it possible to unlock the tip merely by a slight twist.

18 Claims, 2 Drawing Sheets

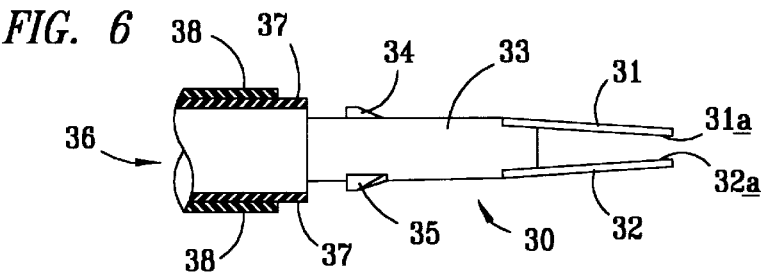
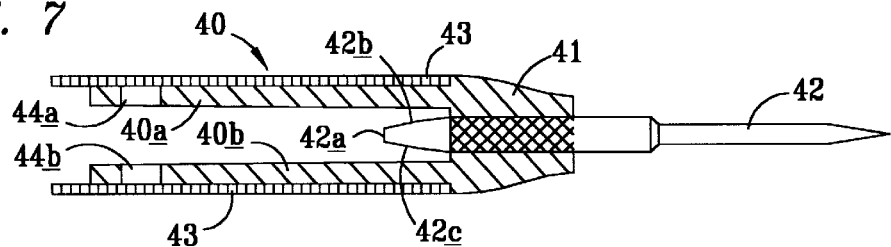
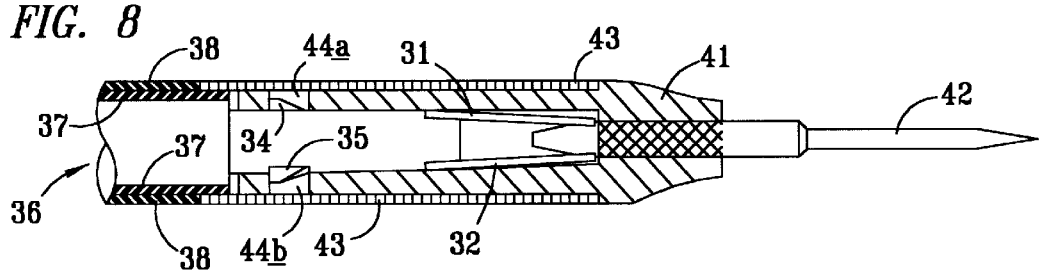
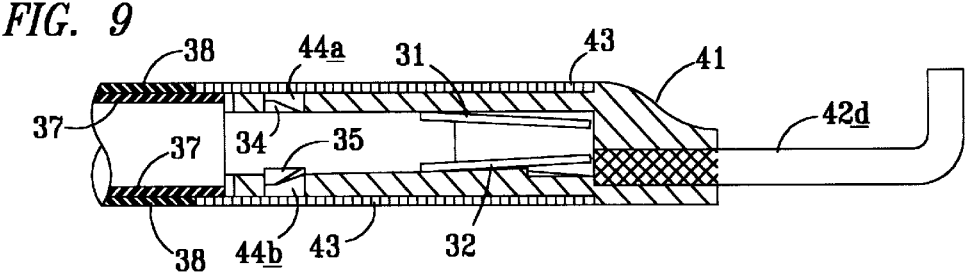
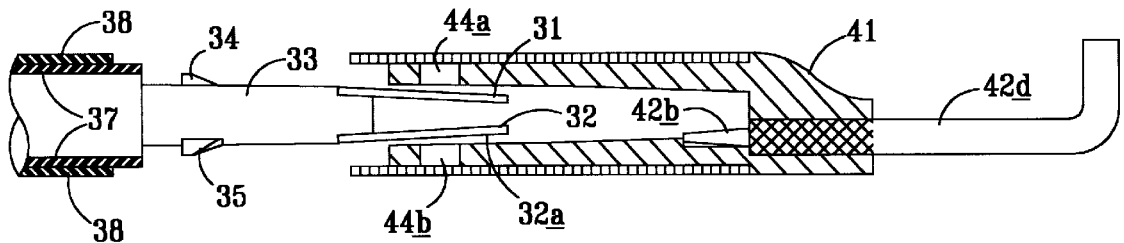

ELECTROSURGICAL ELECTRODE CONNECTOR

This invention relates to electrosurgical electrode connectors and more particularly to quick attachment/detachment connectors that are adapted for facilitating the attachment of working elements such as medical electrodes to members such as electrode holders, handles, or receptacles.

BACKGROUND OF THE INVENTION

As is known to those skilled in the art, there is a high level of concern in medical circles for improving cost effectiveness while maintaining acceptable levels of quality of medical services. One of the factors contributing to cost is the expense of providing and maintaining an acceptable level of cleanliness and sterilization. Techniques such as autoclaving for sterilizing medical equipment is time consuming; and for some medical instruments or parts thereof, it is not practicable. Accordingly, there has been a trend toward disposability of certain instruments. For others, where disposability is costly, it has become customary to make the instruments in parts which may be connected together for use. According to such proposals, parts such as operating handles are preserved and re-used, and other parts such as tips are discarded or are thoroughly sterilized after each use. Still others are sterilized and re-used a few number of times only. An example is that of the electrode disclosed in U.S. patent application Ser. No. 08/342,215 filed Nov. 18, 1994. Other examples of disconnectable parts for medical instruments are those set forth in German Offenlegungsschrift 2,404,764.

BRIEF SUMMARY OF THE INVENTION

The improved connection/disconnection device according to the invention hereof includes a rod-shaped main shaft extending from a handle or other support member. Spaced on opposite sides of the main shaft and extending outwardly therefrom, are a pair of specially shaped pins each having two small vertical surfaces, a non-horizontal surface such as a ramp extending generally downwardly in a direction toward the distal end of the main shaft and a radially curved surface. The connectable element (such as a medical electrode which may be disposable or non-disposable) has a connecting section that includes a tunnel-shaped recess having minutely larger interior dimensions than the corresponding exterior of the main supporting shaft, thus providing for a telescoping fit. On opposite sides of the tunnel shaped recess there are a pair of longitudinally extending slots adapted to partially divide the connectable element into two bifurcated finger-like sections each having a cantilevered spring-like quality. Also disposed in the finger-like sections of the connectable element are two generally rectangular apertures extending through its walls and spaced laterally between the two slots. These two apertures are positioned so as to engage the aforementioned pins when the connectable element is mounted on the shaft. Thus, when connection is made between the shaft and the connectable element, the aforementioned spring-like quality permits the interior surfaces of the finger-like sections to spread apart slightly as they ride up the aforementioned non-horizontal surfaces. When engagement has proceeded to the point where the pins reach the apertures, they snap thereinto, the spring-like force imparted by the finger-like sections retaining them in place until it is desired to achieve disconnection. Disconnection is accomplished by imparting a torque between the shaft and connectable element such as by twisting the connectable element slightly. When this occurs, the finger-like elements are spread slightly by the thrust imparted thereto as the interior surfaces of the finger-like elements ride up the aforementioned radially curved surfaces of the pins.

OBJECTS AND FEATURES OF THE INVENTION

It is one general object of the invention to improve quick disconnect connections.

It is another object of the invention to improve dependability while simplifying quick disconnect connections.

It is yet another object of the invention to facilitate ease of engagement/disengagement and mounting of disposable or non-disposable medical instruments on mountings.

Accordingly, in accordance with one feature of the invention, a pair of specially shaped pins are positioned on opposite sides of a rod-shaped mounting member thus facilitating dependable locking and unlocking of a connecting member thereupon.

In accordance with another feature of the invention, a connectable member having a tunnel-shaped recess adapted to telescope with the rod-shaped mounting member is provided with a pair of longitudinally disposed parallel slots disposed on opposite sides thereby partially dividing the connectable member into two bifurcated sections, providing for cantilevered spring-like action and facilitating telescoping of the connectable member and mounting member into frictionally engaging relationship.

In accordance with still another feature of the invention, the specially shaped pins cooperate with geometries of the connectable member to slightly spring apart the two bifurcated sections as the mounting member and the connectable member are engaged and telescoped thus providing spring force to lock the members together when the parts are fully engaged.

In accordance with yet another feature of the invention, within each of the bifurcated sections there is provided a slot which is adapted for receiving and retaining a corresponding one of the aforementioned specially shaped pins when the parts are fully engaged, thus releaseably locking the parts together when they are fully telescoped.

In accordance with still another feature of the invention, the aforementioned radially shaped surface on each of the two pins is adapted for engagement with an inner surface of the corresponding one of the two bifurcated sections, thereby providing for disconnection by imparting a relative radial torque between the mount and connectable member that results in a force which slightly spreads apart the two bifurcated members to release the pins from the slots and permit disengagement.

These and other objects and features of the invention will be apparent from the following description, by way of example of a preferred embodiment, with reference to the drawing.

BRIEF DESCRIPTION OF THE DRAWING

FIG. 6 is a view, partly in section, depicting an alternate mounting member having a pair of extending electrical contacts;

FIG. 7 is a side sectional view of a disposable electrosurgical implement adapted for engagement and mounting on the mounting member of FIG. 6;

FIG. 8 is a side view, partly in section, depicting the disposable electrosurgical implement of FIG. 7 mounted on the mounting member of FIG. 6;

FIG. 9 is a side view, partly in section, depicting a different electrosurgical implement mounted on the mounting member of FIG. 6; and FIG. 10 is a view depicting the parts of FIG. 9 partly disassembled.

DESCRIPTION OF A PREFERRED EMBODIMENT

Figure 1:
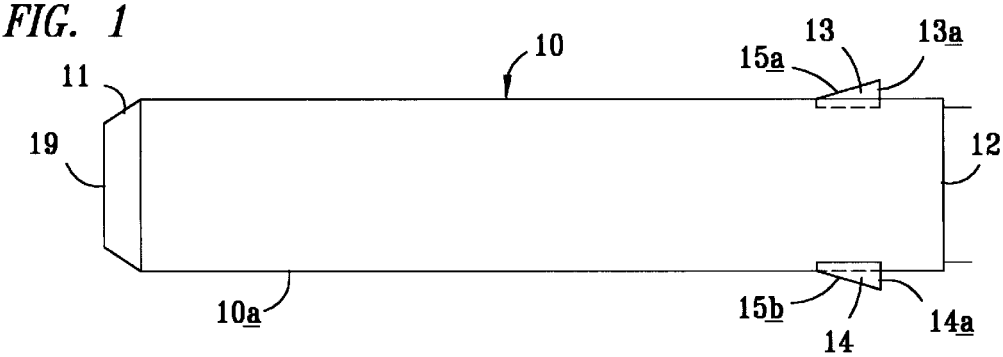
FIG. 1 is a view depicting a mounting shaft with a pair specially shaped locking pins extending outwardly therefrom.

Now turning to the drawing, and more particularly FIG. 1 thereof, it will seen to show a side elevation view of a rod-shaped mounting shaft 10 illustrating the principles of the instant invention. The shaft preferably is generally cylindrical and may include a bevelled surface such as surface 11. Alternatively, surface 11 may be rounded, it being the purpose of surface 11 to facilitate engagement with a mating female part such as that illustrated in FIGS. 4 and 5. Near proximal end 12 there are provided a pair of projecting pins 13 and 14 which include ramps 15a/15b that slope upwardly, but which can also curvilinearly extend upwardly, in the direction of proximal end 12 and terminate at a first pair of vertical cliff surfaces 13a and 14a. Each of these pins is specially shaped as will be evident from FIGS. 1 and 3; and each is either an integral extension of shaft 10 (preferably) or is rigidly affixed thereto. By effectively making the pins integral extensions of shaft 10, cleansing of the shaft and pins is facilitated.

Figure 2:
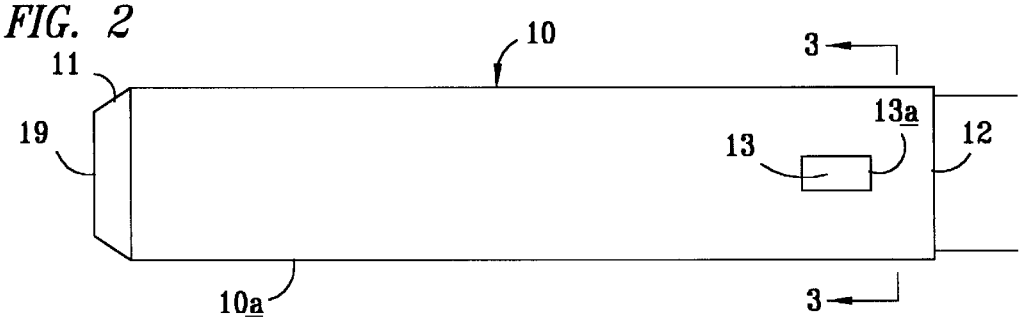
FIG. 2 is a top view of the mounting shaft of FIG. 1.

FIG. 2 is a top view of the cylindrical mounting shaft 10 of FIG. 1. There, it will be seen, are surfaces 10a, 11, proximal end 12, distal end 19 and projecting pin 13.

Figure 3:
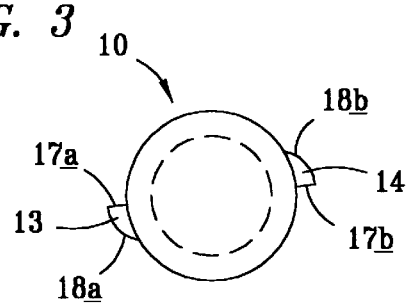
FIG. 3 is a section taken along the section lines 3—3 of FIG. 2.

FIG. 3 is a section taken along the section lines 3—3 of FIG. 2. There, in FIG. 3, are illustrated the specially shaped pins 13 and 14 showing each as having: a second pair of miniature cliff-like vertical surfaces 17a/17b (the first set being those designated 13a/14a in FIG. 1) essentially at right angles to the adjoining surface of mounting shaft 10; and a curved surface (surfaces 18a/18b) at the opposite side and extending upwardly and over to the tops of the cliffs 17a/17b respectively. It will thus be seen that the specially-shaped pins 13 and 14 each have a plurality of surfaces including a sloping ramp 15a/15b, a first cliff-like surface 13a/14a (FIG. 1), a second vertical cliff-like surface 17a/17b (FIG. 3) and a rounded surface 18a/18b.

Figure 4:
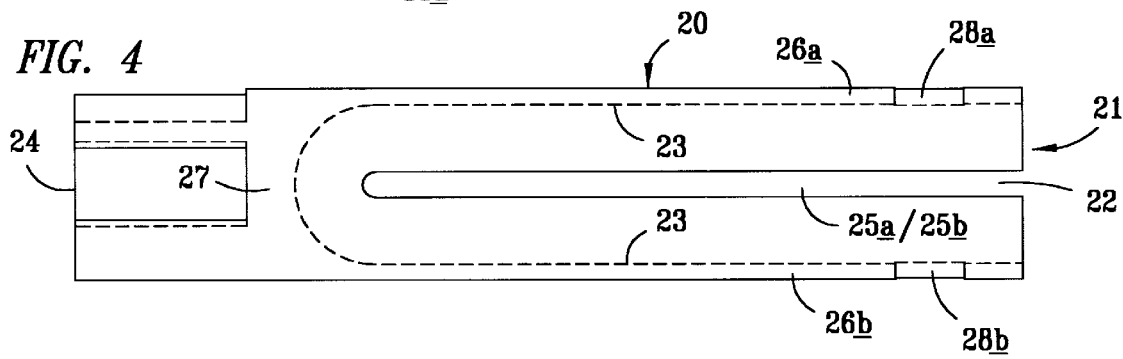
FIG. 4 is a side elevation view of a bifurcated connectable member adapted for telescoping engagement with a mounting shaft such as that depicted in FIGS. 1–3.

As mentioned above, the electrosurgical connector according to the invention includes a connectable member adapted for mounting on the exterior surface of mounting shaft 10. One such connectable member 20 is depicted in FIG. 4 where there is shown beginning at the proximal end 21 thereof a cylindrical recess 22 extending as defined by dashed line 23. As will be evident from the remaining description, recess 22 is adapted for telescoping onto mounting shaft 10. Thus, recess 22 is preferably principally cylindrical except for its distal extremity which is preferably, though not necessarily, rounded as shown. Longitudinally extending from proximal end 21 toward distal end 24 along recess 22 for a predetermined distance less than the full distance between proximal and distal ends 21 and 24 are a pair of slots 25a/25b which divide and bifurcate the proximal portion into two bifurcated sections 26a/26b projecting to proximal end 21 from their joinder to distal end 24 at region 27. Also shown are a pair of apertures 28a/28b which are provided for engaging projecting pins 13 and 14 when connectable member 20 is telescoped into position on mounting shaft 10.

Figure 5:
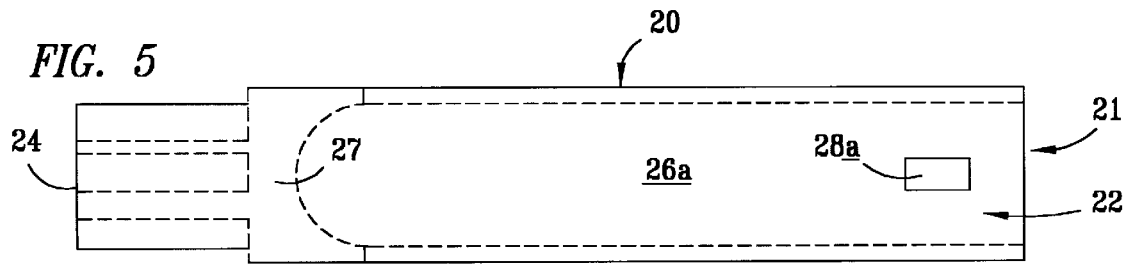
FIG. 5 is a top view of the connectable member of FIG. 4.

FIG. 5 is a top view of the connectable member illustrated in FIG. 4. There, it will be observed, are member 20 with proximal end 21, longitudinally extending tunnel-like recess 22, distal end 24, bifurcated section 26a and aperture 28a.

When it is desired to mount and disengageably lock connectable member 20 onto mounting shaft 10, proximal end 21 of connectable member 20 is brought into alignment with distal end 19 of mounting shaft 10. It is then telescoped thereupon so that the inner surface of member 20 as defined by dashed line 23 loosely and slideably engages outer surface 10a of shaft 10. However, when telescoping has proceeded to a point at which inner surface 23 engages ramps 15a/15b of pins 13 and 14, further axial urging together of the parts results in a slight springing apart of bifurcated parts 26a/26b as the interior surfaces ride up the ramps. After they have reached the upper limit of the ramps and progressed along the interior surfaces of parts 26a/26b to a point where the pins have reached apertures 28a/28b, the pins snap into the apertures, whereupon parts 26a/26b spring back into their quiescent conditions in which they are fitted onto mounting shaft 10.

As mentioned above, when it is desired to disconnect the two parts, disengagement is accomplished by imparting a torque between the mounting shaft 10 and connectable element 20 such as by twisting the connectable element slightly. When this occurs, due to the curved surfaces 18a/18b of the pins, the finger-like elements 26a/26b are spread by the thrust imparted thereto as the pins exit from apertures 28a/28b, the interior surfaces of the finger-like elements riding up the aforementioned radially curved surface 18a/18b of the pins 13 and 14. Disengagement is then completed by urging the connectable element outwardly in a direction along its central axis.

FIG. 6 is a view, partly in section, depicting an alternate mounting member 30 having a pair of extending electrical flexible cantilevered contacts 31 and 32. These are mounted by any conventional means on mounting shaft 33 which generally corresponds to mounting shaft 10 in FIGS. 1–3. Also seen in FIG. 6 are two specially shaped pins 34 an 35 which are similar in shape and function to pins 13 and 14 described above. Also shown are conventional shaft extension 36 with conventional primary and secondary insulating coverings 37 and 38.

FIG. 7 is a side sectional view of a connectable member, e.g., disposable electrosurgical implement 40, adapted for engagement and mounting on the mounting member 30 of FIG. 6. There, it will be seen, are molded polymer section 41 within which there is fixed an electrosurgical electrode tip member 42. At the proximal end 42a, there are provided a pair of sloping surfaces 42b and 42c which are adapted for engaging contacting surfaces 31a and 32a of cantilevered contacts 31 and 32 when electrosurgical implement 40 is telescoped into position on mounting shaft 33 as is shown in FIG. 8. On the exterior of implement 40 is a layer of conventional insulation 43 which circumferentially surrounds the proximal portion of the implement as shown. Also seen in FIG. 7 are apertures 44a and 44b extending through molded polymer 41 which may also extend through insulation 43 or may be covered over, thereby forming small recesses. To avoid repetition and to preserve clarity of presentation, the slots corresponding to slots 25a/25b of FIG. 4 are not shown but are understood to function in like manner. Thus there are provided two bifurcated springy sections 40a and 40b.

Now turning to FIG. 8, the electrosurgical implement 40 is shown in place and disengageably locked to mounting shaft 33. As described above in connection with FIGS. 1–5, this is accomplished by telescoping member 40 onto shaft 33 until it is fully engaged and pins 34 and 35 snapped into place within apertures 44a and 44b. Also as mentioned above, when it is desired to disengage telescoping member 40 from shaft 33, a twist of implement 40 causes spreading of finger-like sections 40a/40b by the pins 34 and 35 (due to their above-described rounded surfaces), thus causing the pins to be released from apertures 44a and 44b and resulting in their unlocking. Member 40 may then be entirely withdrawn from shaft 33 as described above with respect to FIGS. 1–5.

FIG. 9 is seen to be a side view, partly in section, depicting a different electrosurgical implement mounted on the mounting member of FIG. 6; and FIG. 10 is also a side view but showing the parts partly disassembled. However except for geometry and placement of electrode tip 42d, the off-center axis thereof with respect to the central axis of the mounting, and the electrical contact between surface 32a and surface 42b (FIG. 10) the parts are similar to those of FIGS. 6, 7 and 8, and accordingly operate similarly. Attention is directed, however, to the difference in the way electrical contact is made. In the off-center line arrangement of FIGS. 9 and 10, electrical contact is made between surfaces 32a and 42b.

It will now be evident that there has herein been described an improved quick-connect-disconnect mounting that is particularly adapted for medical and attendant uses in which a mounting portion is reusable while a tip portion is disposable.

Although the invention hereof has been described by way of a preferred embodiment, it will be evident that other adaptations and modifications may be employed without departing from the spirit and scope thereof. For example, one or more additional pins could be employed, and the total number of pins then deployed at spaced intervals about the exterior of the mounting shaft. Moreover, the parts could be made with at least partially non-cylindrical geometries.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An electrosurgical electrode connector comprising a mounting member having an extending shaft with a circumferential exterior surface, said extending shaft including:
   (a) a proximal end and a distal end;
   (b) a first pin having a first plurality of outer surfaces, said first pin being affixed to said circumferential exterior surface of said shaft at a first location displaced from said distal end toward said proximal end;
   (c) a second pin having a second plurality of outer surfaces similar to said first plurality of outer surfaces, said second pin being affixed to said circumferential exterior surface of said shaft at a second location displaced from said distal end toward said proximal end, said first and said second pluralities of said outer surfaces of said first and said second pins each having a rounded surface, a sloping ramp starting at said exterior surface of said shaft and an essentially perpendicular cliff extending to said exterior surface of said shaft, said rounded surface extending directly and uninterruptedly between the top of said cliff and said circumferential exterior surface of said extending shaft.

2. An electrosurgical electrode connector according to claim 1 wherein said sloping ramp is essentially rectilinear.

3. An electrosurgical electrode connector according to claim 1 wherein said ramp is disposed on said shaft so that said ramp extends upwardly in the direction of said proximal end of said shaft.

4. An electrosurgical electrode connector according to claim 1 wherein each of said pins includes another cliff essentially at right angles to said first cliff and wherein said rounded surface begins on an opposite side of said pin from said another cliff.

5. An electrosurgical electrode connector according to claim 1 wherein said first and said second pins are integral with said extending shaft.

6. An electrosurgical electrode connector according to claim 5 wherein said cliff is essentially vertical with respect to adjacent surface of said shaft.

7. An electrosurgical electrode connector comprising:
   (a) A mounting member having an extending shaft with a circumferential exterior surface, said extending shaft including:
      (i) a proximal end and a distal end;
      (ii) a first pin having a first plurality of outer surfaces, said first pin being affixed to said exterior surface of said shaft at a first location displaced from said distal end toward said proximal end;
      (iii) a second pin having a second plurality of outer surfaces similar to said first plurality of outer surfaces, said second pin being affixed to said circumferential exterior surface of said shaft at a second location displaced from said distal end toward said proximal end, said first and said second pluralities of said outer surfaces of said first and said second pins each having a rounded surface, a ramp starting at said exterior surface of said shaft, and an essentially perpendicular cliff extending to said exterior surface of said shaft, said rounded surface extending directly and uninterruptedly between the top of said cliff and said circumferential exterior surface of said extending shaft;
   (b) a connectable member for mounting on said exterior surface of said extending shaft, said connectable member having a proximal end and a distal end, said connectable member having an elongated tunnel-like recess at said proximal end of said connectable member, said elongated tunnel-like recess being sized for telescoping engagement with said exterior surface of said extending shaft; and
   (c) locking means including said pins effective when said connectable member is telescoped onto said extending shaft for disengageably locking said connectable member onto said extending shaft.

8. An electrosurgical electrode connector according to claim 7 wherein said ramp is essentially rectilinear.

9. An electrosurgical electrode connector according to claim 7 wherein said ramp is disposed on said shaft so that said ramp extends upwardly in the direction of said proximal end of said shaft.

10. An electrosurgical electrode connector according to claim 7 wherein each of said pins includes another cliff essentially at right angles to said first cliff and wherein said rounded surface begins on an opposite side of said pin from said another cliff.

11. An electrosurgical electrode connector according to claim 7 in which said first and said second pins are positioned circumferentially on opposite sides of said circumferential exterior surface of said shaft.

12. An electrosurgical electrode connector according to claim 7 in which said mounting member is non-disposable and said connectable member is disposable.

13. An electrosurgical electrode connector according to claim 7 wherein said locking means includes spring means for urging said connectable member into locking engagement with said extending shaft when said connectable member is telescoped onto said extending shaft.

14. An electrosurgical electrode connector according to claim 13 wherein said cliff is essentially perpendicular with respect to adjacent surface of said shaft.

15. An electrosurgical electrode connector according to claim 7 wherein said connectable member includes:
   (i) a proximal end and a distal end; and
   (ii) slots extending from said proximal end forward toward said distal end a predetermined distance less than the entire distance between said proximal and said distal ends to define first and second bifurcated walls of said tunnel-like recess.

16. An electrosurgical electrode connector according to claim 15 wherein said first wall includes a first aperture therein, said second wall includes a second aperture therein, said first and said second apertures being positioned essentially circumferentially on opposite sides of said recess.

17. An electrosurgical electrode connector according to claim 16 wherein said locking means is effective to extend said first pin into said first aperture and said second pin into said second aperture thereby to disengagably lock said connectable member to said mounting member.

18. An electrosurgical electrode connector comprising:
   (a) A mounting member having an extending shaft with a circumferential exterior surface, said extending shaft including:
      (i) a proximal end and a distal end;
      (ii) a first pin having a first plurality of outer surfaces, said first pin being affixed to said exterior circumferential surface of said shaft at a first location displaced from said distal end toward said proximal end;
      (iii) a second pin having a second plurality of outer surfaces similar to said first plurality of outer surfaces, said second pin being affixed to said circumferential exterior surface of said shaft at a second location displaced from said distal end toward said proximal end, said first and said second pluralities of said outer surfaces of said first and said second pins each having:
         (1) a rounded surface,
         (2) a ramp rectilinear surface sloping upwardly toward said proximal end of said extending shaft,
         (3) a first cliff having a planar surface essentially perpendicular with respect to immediately adjacent surface of said shaft, said rounded surface extending directly and uninterruptedly between the top of said cliff and said circumferential exterior surface of said extending shaft,
         (4) a second cliff having a planar surface essentially perpendicular with respect to immediately adjacent surface of said shaft, the plane of said second cliff being essentially at right angles to the plane of said first cliff,
      said rounded surface being disposed on a side of said pin beginning at an opposite side to that of said second cliff, said first and said second pins being positioned circumferentially on opposite sides of said exterior cylindrical surface;
   (b) a connectable member adapted for mounting on said exterior surface of said extending shaft, said connectable member having a proximal end and a distal end, a tunnel-like recess at said proximal end of said connectable member, said tunnel-like recess having a slot extending from said proximal end of said connectable member forward toward said distal end of said connectable member a predetermined distance less than the entire distance between said proximal and said distal ends of said connectable member to define first and second bifurcated walls of said tunnel-like recess and adapting said connectable member for telescoping engagement with said exterior surface of said extending shaft, said first wall having a first aperture therein and said second wall having a second aperture therein; and
   (c) locking means including said pins and said apertures effective when said connectable member is telescoped onto said extending shaft for disengageably locking said connectable member onto said extending shaft.

\* \* \* \* \*